US009451974B2

(12) United States Patent
Cinquin et al.

(10) Patent No.: US 9,451,974 B2
(45) Date of Patent: Sep. 27, 2016

(54) MODULAR SURGICAL TOOL

(75) Inventors: Philippe Cinquin, St. Nazaire Les Eymes (FR); Juan Carlos Avila Vilchis, Toluca (MX); Nabil Zemiti, Montpellier (FR); Adriana Herlinda Vilchis Gonzalez, Toluca (MX)

(73) Assignee: Universite Joseph Fourier—Grenoble 1, St. Martin d'Hères (FR)

( * ) Notice: Subject to any disclaimer, the term of this patent is extended or adjusted under 35 U.S.C. 154(b) by 719 days.

(21) Appl. No.: 13/056,273

(22) PCT Filed: Jul. 28, 2009

(86) PCT No.: PCT/EP2009/059771
§ 371 (c)(1),
(2), (4) Date: Jan. 27, 2011

(87) PCT Pub. No.: WO2010/012748
PCT Pub. Date: Feb. 4, 2010

(65) Prior Publication Data
US 2011/0130787 A1    Jun. 2, 2011

(30) Foreign Application Priority Data

Jul. 29, 2008    (FR) ..................... 08 55188

(51) Int. Cl.
*A61B 17/00*    (2006.01)
*A61B 17/29*    (2006.01)

(52) U.S. Cl.
CPC .......... *A61B 17/29* (2013.01); *A61B 17/00234* (2013.01); *A61B 34/30* (2016.02);
(Continued)

(58) Field of Classification Search
CPC ................. A61B 2019/2242; A61B 19/2203; A61B 19/22; A61B 2019/2238
USPC ................................................ 606/130, 205
See application file for complete search history.

(56) References Cited

U.S. PATENT DOCUMENTS 5,352,219 A    10/1994 Reddy
5,399,951 A    3/1995 Lavallee et al.
(Continued)

FOREIGN PATENT DOCUMENTS

FR    2 875 123    3/2006
WO    WO 98/49951    11/1998
(Continued)

OTHER PUBLICATIONS

Takayam et al., "Detachable-Fingered Hands for Manipulation of Large Internal Organs in Laparoscopic Surgery", Apr. 2007, 2007 IEEE International Conference on Robotics and Automation, pp. 244-249.*

(Continued)

*Primary Examiner* — Tuan V Nguyen
*Assistant Examiner* — Kevin Everage
(74) *Attorney, Agent, or Firm* — Harness, Dickey & Pierce, P.L.C.

(57) ABSTRACT

The present disclosure relates to a minimally invasive surgical procedure device including a set for forming a modular surgical tool, the set including a carrier shaft and a plurality of functional modules, in which the each functional module has means for rigid connection to the carrier shaft and/or to another functional module and has dimensions suitable for insertion into the body of a patient through a trocar, wherein the device is characterized in that: —each functional module has at least one degree of rotational or translational freedom and/or a functional end-piece such as a forceps, hook or a scalpel, —the carrier shaft and/or the functional modules include means for actuating the functional modules according to the respective degree of freedom thereof and/or the respective function thereof, and in that the device includes an electromechanical interface capable of controlling the actuating of the assembled functional modules forming the tool.

21 Claims, 5 Drawing Sheets

(52) U.S. Cl.
CPC ............... *A61B2017/00265* (2013.01); *A61B 2017/00477* (2013.01); *A61B 2017/00544* (2013.01); *A61B 2017/2931* (2013.01); *Y10T 29/49826* (2015.01)

(56) References Cited

U.S. PATENT DOCUMENTS

| | | | |
|---|---|---|---|
| 5,529,159 | A | 6/1996 | Troccaz |
| 5,752,972 | A | 5/1998 | Hoogeboom |
| 5,810,716 | A | 9/1998 | Mukherjee et al. |
| 6,074,408 | A | 6/2000 | Freeman |
| 6,309,403 | B1 | 10/2001 | Minor et al. |
| 6,385,475 | B1 | 5/2002 | Cinquin et al. |
| 6,436,107 | B1 | 8/2002 | Wang et al. |
| 6,685,698 | B2 | 2/2004 | Morley et al. |
| 6,915,150 | B2 | 7/2005 | Cinquin et al. |
| 6,932,089 | B1 | 8/2005 | Cinquin et al. |
| 7,033,360 | B2 | 4/2006 | Cinquin et al. |
| 7,086,309 | B2 | 8/2006 | Stoianovici et al. |
| 7,150,751 | B2 | 12/2006 | Lechot |
| 7,199,545 | B2 | 4/2007 | Oleynikov et al. |
| 7,208,005 | B2 | 4/2007 | Frecker et al. |
| 7,214,230 | B2 | 5/2007 | Brock et al. |
| 7,247,116 | B2 | 7/2007 | Stoianovici et al. |
| 7,752,972 | B1 | 7/2010 | Baker et al. |
| 2002/0082518 | A1 | 6/2002 | Weiss et al. |
| 2003/0055436 | A1 | 3/2003 | Daum et al. |
| 2004/0133189 | A1 | 7/2004 | Sakurai |
| 2006/0100501 | A1 | 5/2006 | Berkelman et al. |
| 2007/0034046 | A1 | 2/2007 | Stoianovici et al. |
| 2009/0054909 | A1* | 2/2009 | Farritor .............. A61B 19/22 606/130 |
| 2009/0118610 | A1 | 5/2009 | Karmarkar et al. |
| 2009/0171373 | A1* | 7/2009 | Farritor ............ A61B 19/2203 606/130 |

FOREIGN PATENT DOCUMENTS

| | | |
|---|---|---|
| WO | WO 03/094579 | 11/2003 |
| WO | WO 2007/064739 | 6/2007 |
| WO | WO 2010/012744 | 2/2010 |

OTHER PUBLICATIONS

Takayama, T. et al.; "Detachable-Fingered Hands for Manipulation of Large Internal Organs in Laparoscopic Surgery;" Robotics and Automation, 2007; International Conference on IEEE, PI; Apr. 1, 2007; pp. 244-249, ISBN: 978-1-4244-0601-2; p. 245, col. 1, paragraph 2; figures 1,2; p. 244, col. 1, paragraph 3—col. 2, paragraph 1.

Guthart, G.S. et al.; "The intuitive telesurgery system: Overview and application;" IEEE International Conference on Robotics and Automation—ICRA, pp. 618-621, 2000.

Vilchis Gonzales, A. et al.; "TER: A system for robotic tele-echography, in proceedings of Medical Image Computing and Computer Assisted Intervention (MICCAI);" Lecture notes in Computer Science, Springer Verlag, vol. 2208, pp. 326-334, 2001.

çavuşoğlu, M. et al.; "Robotics for telesurgery: Second generation Berkeley/UCSF laparoscopic telesurgical workstation and looking towards the future applications;" The Industrial Robot: Special Issueon medical robotics, vol. 30, No. 1, pp. 22-29, 2003.

Damiano, R.J. et al.; "Initial prospective multicenter clinical trial of robotically-assisted coronary artery bypass graphting;" Annals of thoracic surgery, vol. 72, pp. 1263-1269, 2001.

Seibold, U. et al.; "Sensorized and actuated instruments for minimally invasive robotic surgery;" Eurohaptics International Conference, pp. 482-485, 2004.

Taylor, R.H. et al.; "Medical robotics in computer-integrated surgery;" IEEE Transactions on Robotics and Automation, vol. 19, No. 5, pp. 765-781, 2003.

Masamune, K. et al.; "System for robotically assisted percutaneous procedures with computed tomography guidance;" Journal of Computer Aided Surgery, vol. 6, No. 6, pp. 370-383, 2001.

Patriciu, A. et al.; "Robotic kidney and spine percutaneous procedures using a new laser-based CT registration method, in proceedings of Medical Image Computing and Computer Assisted Intervention (MICCAI);" Lecture notes in Computer Science, Springer Verlag, vol. 2208, pp. 249-257, 2001.

Chinzei, K. et al.; "MR compatible surgical assist robot: System integration and preliminary feasibility study, in proceedings of Medical Image Computing and Computer Assisted Intervention (MICCAI);" Lecture notes in Computer Science, Springer Verlag, vol. 1935, pp. 921-930, 2000.

Taillant, E. et al.; "CT and MR compatible light puncture robot : Architectural design and first experiments, in proceedings of Medical Image Computing and Computer Assisted Intervention (MICCAI);" Lecture notes in Computer Science, Springer Verlag, vol. 3216, pp. 145-152, 2004.

Berkelman, P. et al.; "Design, control and testing of a novel compact laparoscopic endoscope manipulator;" Journal of Systems and Control Engineering, vol. 27, No. 14, pp. 329-341, 2003.

Hata, N. et al.; "Needle guiding robot with five-bar linkage for MR-guided thermotherapy of liver tumor, in proceedings of Medical Image Computing and Computer Assisted Intervention (MICCAI);" Lecture notes in Computer Science, Springer Verlag, vol. 3217, pp. 161-168, 2004.

Koseki, Y. et al.; "Precise evaluation of positioning repeatability of MR-compatible manipulator inside MRI, in proceedings of Medical Image Computing and Computer Assisted Intervention (MICCAI);" Lecture notes in Computer Science, Springer Verlag, vol. 3217, pp. 192-199, 2004.

Koseki, Y. et al.; "Robotic assist for MR-guided surgery using leverage and parallelepiped mechanism, in proceedings of Medical Image Computing and Computer Assisted Intervention (MICCAI);" Lecture notes in Computer Science, Springer Verlag, vol. 1935, pp. 940-948, 2000.

Nakamura, R. et al.; "Development of a sterilizable MR-compatible manipulator for stereotactic neurosurgery;" International Congress on Computer Assisted Radiology and Surgery, pp. 1019, 1999.

Maurin, B. et al.: "A parallel robotic system with force sensors for percutaneous procedures ubder CT-guidace, in proceedings of Medical Image Computing and Computer Assisted Intervention (MICCAI);" Lecture notes in Computer Science, Springer Verlag, vol. 3217, pp. 176-183, 2004.

Daerden, F. et al.; "Pneumatic artificial muscles: Actuators for robotics and automation;" European Journal of Mechanical and Environmental Engineering, vol. 47, No. 1, pp. 11-21, 2002.

Stoianovici, D. et al.; "A new type of motor: Pneumatic step motor;" IEEE/ASME Transactions on Mechatronics, vol. 12, No. 1, pp. 98-106, 2007.

Patriciu, A. et al.; "Automatic brachytherapy seed placement under MRI guidance;" IEEE Transactions on Biomedical Engineering, vol. 54, No. 8, pp. 1499-1506, 2007.

Gassert, R. et al.; "MRI/fMRI-Compatible robotic system with force feedback for interaction with human motion;" IEEE/ASME Transactions on Mechatronics, vol. 11, No. 2, pp. 216-224, Apr. 2006.

Christoforou, E.G. et al.; "Manipulator for magnetic resonance imaging guided interventions: Design, prototype and feasibility;" IEEE International Conference on Robotics and Automation, pp. 3838-3843, 2006.

Tsekos, N.V. et al.; "Magnetic resonance-compatible robotics and mechatronics systems for image-guided interventions and rehabilitation: A review study;" Annual Review of Biomedical Engineering, vol. 9, pp. 351-387, 2007.

DiMaio, S.P. et al.; "A system for MRI-guided prostate interventions;" IEEE/RAS-EMBS International Conference on Biomedical Robotics and Mechatronics, pp. 68-73, 2006.

Webster, R.J. III et al.; "Design considerations for robotic needle steering;" IEEE International Conference on Robotics and Automation, pp. 3599-3605, 2005.

V. Falk, et al., "Endoscopic Computer-Enhanced Beating Heart Coronary Artery Bypass Grafting, Annals of Thoracic Surgery", vol. 70, pp. 2029-2033, 2000.

(56) References Cited

OTHER PUBLICATIONS

R. Howe et al., "Robotics for Surgery, Annual Review of Biomedical Engineering", vol. 01. pp. 211-240, 1999.
H. Rininsland, Artemis. "A Manipulator for Cardiac Surgery" European Journal of Cardiothoracic Surgery, 16(Suppl 2), pp. S106-S111, 1999.
R. Nakamura, et al., "Multi-DOF Forceps Manipulator System for Laparoscopic Surgery—Mechanism Miniaturized and Evaluation of New Interface-", in Proc; of Fourth International Conference on Medical Image Computing and Computer Assisted Interventions (MICCAI), pp. 606-613, 2001.
A. Faraz et al., "Engineering Approaches to Mechanical and Robotic Design for Minimally Invasive Surgeries", Kluwer Academic Publishers, 2000.
J. W. Cannon, et al., "Port Placement Planning in Robot-Assisted Coronary Artery Bypass, IEEE transactions on Robotics and Automation", vol. 19, No. 5, pp. 912-917, 2003.
P. Breedveld et al., "Development of the Endo-Periscope, Minimally Invasive Therapy and Allied Technologies", vol. 10, No. 6, pp. 315-322, 2001.
K. Ikuta and M. Nokata, "Two-Lead-Wire Drive for Multi-Micro Actuators", in Proc of the IEEE International Conference on Robotics and Automation (ICRA), pp. 2378-2384, 1999.
K. Ikuta et al., "Development of Remote Micro-Surgery Robot and New Surgical Procedure for Deep and Narrow Space", in Proc of the IEEE International Conference on Robotics and Automation (ICRA), pp. 1103-1108, 2003.
H. Das et al., "Robot Assisted Microsurgery Development at JPL", Workshop on Medical Application of Virtual Reality, 1997.
P. Dario et al., "Smart Surgical Tools and Augmenting Devices", IEEE Transactions on Robotics and Automation, vol. 19, No. 5, pp. 782-792, 2003.
F. Van Meer et al., "A Disposable Plastic Compact Wrist for Smart Minimally Invasive Surgical Tools", Intelligent Robos and Systems conference, pp. 919-924, 2005.
S. Park et al., "Trocar-Less Instrumentation for Laparoscopy, Annals of Surgery", vol. 245, No. 3, pp. 379-384, 2007.
M. E. Rentschler et al., "An In Vivo Mobile Robot for Surgical Vision and Task Assistance", ASME Journal of Medical Devices, vol. 1, pp. 23-29, 2007.
V. R. C. Kode et al., "Design and Characterization of a Novel Hybrid Actuator Using Shape Memory Alloy and DC Micromotor for Minimally Invasive Surgery Applictions", IEEE/ASME Transactions on Mechatronics, vol. 12, No. 4, pp. 455-464, 2007.
G. Tholey and J. P. Desai, "A modular, automated laparoscopic grasper with three-dimensional force measurement capability", IEEE International Conference on Robotics and Automation, pp. 250-255, 2007.

* cited by examiner

MODULAR SURGICAL TOOL

CROSS-REFERENCE TO RELATED APPLICATIONS

This application is a U.S. National Phase entry of International Application No. PCT/EP2009/059771, filed on Jul. 28, 2009, which claims priority to French Application Serial No. 0855188, filed on Jul. 29, 2008, both of which are incorporated by reference herein.

FIELD OF THE INVENTION

The present invention relates to a modular surgical tool for minimally invasive surgery.

BACKGROUND OF THE INVENTION

Minimally invasive surgery is a surgical approach aimed at intervening inside the body of a patient by accessing organs on which intervention must be made, by making a minimum number of openings in the body. For this purpose, the surgeon makes small-size incisions in the body of the patient, into which he inserts trocars intended for passage of instruments and display apparatus, such as an endoscope or a laparoscope to better observe the intervention zone. The trocars which permits passage of display apparatus are called "optical trocars" and generally have inner diameters of 10 mm or 12 mm. Trocars which allow passage of surgical instruments are called "operating trocars" and generally have inner diameters of 5 mm, given that operating trocars of inner diameter of 8 mm, 10 mm or 12 mm can also be used if the operation requires them.

Due to the advantages of this surgical technique for the patient, especially in terms of patient comfort, rapid post-operative recovery, and short hospitalisation, numerous tools have been developed to allow the surgeon to make gestures as precise as those made in open surgery where he benefits from wider access to the intervention region. But tools proposed to date still have drawbacks which hamper progress of minimally invasive surgery. Of these problems, the lack of dexterity or minimal mobility offered by current tools have been cited by doctors.

Robotic tools with internal mobilities, that is, having different degrees of freedom actuatable inside the body of the patient, exist today in a clinical routine (instruments of the DaVinci robot) or in the form of a research laboratory prototype. For insertion of these tools via conventional operative trocars, actuation of internal mobilities of these tools is done by way of remote means (for example, cables, links, tension wires, springs and belts, pulled by actuators placed on the proximal part of the instrument). These actuation devices result in substantial bulk outside the patient, around the surgeon.

Another solution consists of executing the internal mobilities by using direct actuations (that is, mini-motors placed in the distal part of the instrument). For technological reasons (size/power of motors compromise), the resulting tool is very bulky and cannot pass through conventional operative trocars. The use of trocars of greater diameter becomes necessary, which cancels out the minimally invasive and non-traumatising character of the surgical procedure. Also, modularity in design of a tool or medical system has been taken into account in a number of works.

For example, U.S. Pat. No. 6,074,408 refers to a disassemblable modular medical instrument to allow for easier cleaning and replacement of faulty components. Its actuation is based on control by internal cable. The document WO 98/49 951 as such describes a modular surgical instrument allowing interchangeability of the tool due to a ratchet and pawl system. U.S. Pat. No. 7,150,751 refers to the design of a connector for a modular tool.

However, these systems, although modular, have been designed for an assembly external to the body of the patient. In fact, the tool is first fully assembled and then introduced into the body of the patient to carry out the task for which it was designed. This supposes either the use of trocars of considerable diameter for passage of these tools, with harmful consequences to postoperative follow-up, or the design of small-footprint tools which can pass through trocars of lesser diameter, though to the detriment of degrees of freedom.

A number of works has proposed original architectures for medical tools such as endoscopes or other surgical tools, where memory-form alloys are sometimes used, in the ongoing attempt to improve dexterity of the doctor as he carries out surgical gestures. An orientation device with three degrees of freedom and actuated by cables is the subject matter of U.S. Pat. No. 6,685,698.

The article by T. Takayama, T. Omata, T. Futami, H. Akamatsu, T. Ohya, K. Kojima, K. Takase and N. Tanaka ("Detachable-fingered hands for manipulation of large internal organs in laparoscopic surgery", Proc. of International Conference on Robotics and Automation (ICRA), pp. 244-249, 2007), describes as such the assembly, inside the abdomen, of mechanical fingers constituting a "hand", the function of which is to grip, manipulate or push large internal organs. However, in this device, the number of fingers is restricted to three. Also, their actuation is done mechanically by cables, by manual action of the surgeon exerted on the proximal part of the instrument. It is understood that the number of degrees of freedom generally presented by existing instruments for minimally invasive surgery is too low, and that their actuation by cables results in substantial bulk outside the patient.

A first aim of the invention is to design a modular tool with internal mobilities—that is, which can give the surgeon all the degrees of freedom he needs—and which at the same time can be easily assembled and disassembled. Another aim of the invention is to provide a modular tool of sufficiently small dimensions so that it can be inserted into the human body via an opening of minimal diameter, to limit postoperative consequences for the patient. Another aim of the invention is to allow use of a non-remote power source to prevent actuation by cables causing considerable mechanical stress. Finally, the modular tool should be able to be adapted for use in a robotic system.

SUMMARY

The invention proposes a system capable of carrying out the internal mobilities of the tool with a modular system using direct actuation while retaining the non-traumatising and minimally invasive character of a surgical procedure. In keeping with the invention, a minimally invasive surgical intervention device is proposed, comprising a set for forming a modular surgical tool, said set comprising a carrier shaft and a plurality of functional modules, in which each functional module has attachment means to the carrier shaft and/or to another functional module and has appropriate dimensions for insertion into the body of a patient via a trocar, said device being characterised in that:

each functional module has at least one degree of freedom in rotation or in translation and/or a functional end-piece such as forceps, a hook, a scalpel, the carrier shaft and/or the functional modules comprise actuation means of said functional modules according to their degree of freedom and/or their respective function, and in that said device comprises an electromechanical interface capable of controlling actuation of the assembled functional modules forming the tool.

In a particularly advantageous manner, each functional module has at least one degree of freedom in rotation or in translation, and/or a functional end-piece such as forceps, a hook, and a scalpel. The attachment means comprise complementary male and female parts and/or adhesion surfaces by magnetic contact. The carrier shaft and/or the functional modules preferably comprise means for powering and for controlling said functional modules.

According to an embodiment, the carrier shaft has a diameter less than or equal to 8 mm, and each functional module has at least one dimension less than or equal to 12 mm. The device comprises a first trocar having an inner diameter less than or equal to 8 mm for insertion of the shaft and a second trocar having an inner diameter less than or equal to 12 mm for insertion of functional modules. According to a particular embodiment, the device comprises imaging means of the interior of the body of the patient, such as an endoscope or laparoscope.

Advantageously, the device further comprises means for manipulating each functional module in the body of the patient. Said handling means comprise for example forceps connected to the imaging means, a magnet having a hollow cylindrical shape and capable of being mounted on the imaging means without blocking the visual field, or forceps inserted via a third trocar.

Another object of the invention relates to a process for assembling a modular surgical tool, said tool comprising at least one functional module on a carrier shaft, said process being characterised in that it comprises the following steps:
(a) introduction of the carrier shaft in a first trocar installed previously in the body of a patient;
(b) passage of a functional module, in a second trocar installed previously in the body of a patient,
(c) assembly of said functional module on the carrier shaft. Step (b) advantageously comprises successive passage of a plurality of functional modules, the last of which has a functional end-piece, and step (c) comprises successive assembly of said functional modules, such that the assembled tool has at its distal end said functional end-piece. In between steps (b) and (c), the process comprises a handling step of functional modules to guide them from the outlet of the second trocar to the carrier shaft.

BRIEF DESCRIPTION OF FIGURES

Other characteristics and advantages of the invention will emerge from the following detailed description, in reference to the attached diagrams, in which.

DETAILED DESCRIPTION OF THE INVENTION

Surgical Intervention Device

Figure 1:
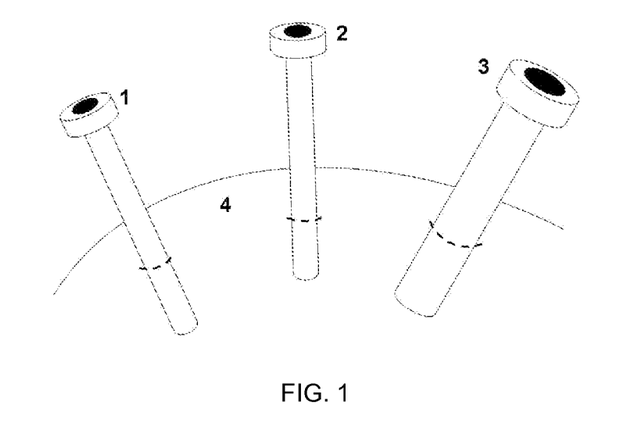
FIG. 1 schematically illustrates installation of trocars in the abdomen of a patient within the scope of minimally invasive surgical intervention.

During minimally invasive surgical intervention made in the abdominal zone (or laparoscopy), a trocar 1, a trocar 2, and a trocar 3 are placed in the abdomen 4 of a patient, as shown in FIG. 1. The trocars 1 and 2 generally have an inner diameter of less than or equal to 8 mm (operating trocar) and the trocar 3 (optical trocar) has an inner diameter of less than or equal to 12 mm. The trocars 1 and 2 allow use of surgical tools such as forceps and the trocar 3 allows use of a laparoscope, for example.

Figure 2:
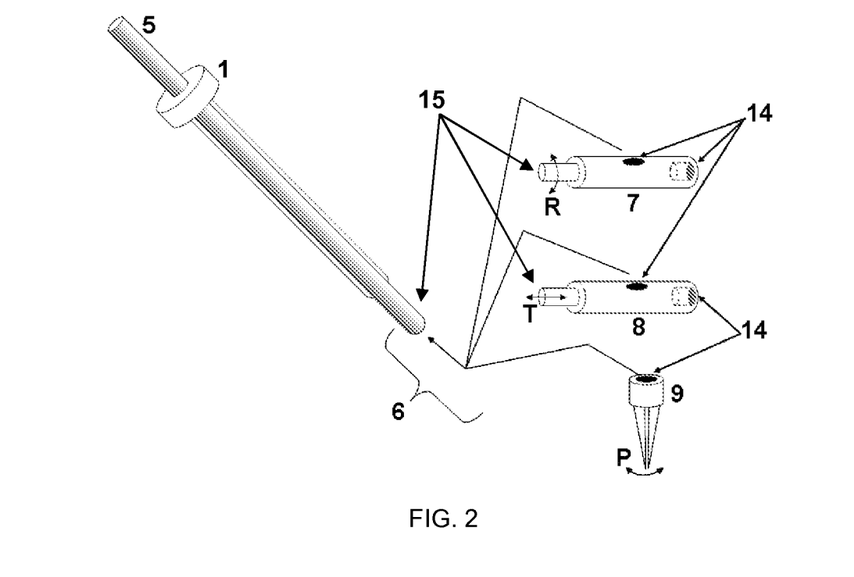
FIG. 2 illustrates a set of functional modules for assembling the modular surgical tool according to the invention.

FIG. 2 shows the trocar 1 divided into its lower part and the carrier shaft 5 of the surgical tool, the distal part 6 of which is to receive functional modules inside the abdomen of the patient. The modular surgical tool according to the invention is in fact assembled from a set of functional modules capable of being connected to the carrier shaft or to another functional module. Modular in this text means that the tool is assembled case by case with the degrees of freedom or the functions preferred by the surgeon. It is also specified in this text that a degree of freedom is associated with translation or rotation; the operating movements of the tool (for example opening and closing of forceps) are not considered as degrees of freedom.

The shaft 5 serves as a base for assembly/disassembly of a series of modules belonging to one of the following classes: module having a degree of freedom in rotation (or "rotation module") 7, module having a degree of freedom in translation (or "translation module") 8 or module having a functional end-piece, such as forceps module 9. Of course, the functional end-piece can be any instrument which the surgeon may need during intervention, such as for example a hook, a scalpel, a needle, etc. For this purpose, each module has means for being connected to the carrier shaft or to another module. For example, each module can have a female form such as the orifice 14 shown in FIG. 2, this female form being capable of being fitted in and held on a male form 15 complementary to the carrier shaft 5 or another functional module (a motor shaft, for example).

The modules with functional end-piece which are designed to form the end of the modular tool can simply have an orifice 14. Of course, any other form of attachment means is feasible (complementary male/female forms, clips, screws, magnetic means, electromechanical means, etc.). Also, the attachment means are likewise designed to enable transmission of energy and operating commands to each of the modules.

In particular, the tool is controlled from an electromechanical interface, such as a haptic interface, by means of which the surgeon indicates selected movements and which transmits via a controller control signals to each functional module. The carrier shaft 5 must be designed such that its inner part contains transmission supports (electric, fluid or other) for power feed and for information exchange and control signals between the actuators, the sensors and the system controller. Also, the proximal part (external to the surgical cavity) and distal part (in the surgical cavity) of the carrier shaft 5 comprise contactors or connectors ensuring links between both the shaft and the functional modules (actuators) and the carrier shaft and the controller.

According to a variant, it is possible for each of the functional modules to have its own power supply means, for example in the form of miniature batteries. Also, according to another embodiment of the invention, the carrier shaft 5 is a simple passive shaft and power supply, information exchange and control signals between the actuators, the sensors and the system controller are sent wirelessly (radio frequency, ultrasound, Bluetooth, Wifi, induction, magnetic, etc.).

The orifice 14 helping with installation of the modules can be located on the most appropriate face of each module. If, as in FIG. 2, the functional module has a cylindrical shape, for example, the orifice 14 can be placed in the base or in the lateral surface of the cylinder. If the functional module is a cube, the orifice 14 can be placed on one of the five surfaces of the cube not containing the motor axis of the module. Alternatively, adhesion surfaces by magnetic contact will be used in place of complementary male and female parts.

The length of each module can be over 12 mm; however, its width is to be under 12 mm as assembly of the tool is based on use of the trocar 3 of inner diameter less than or equal to 12 mm to allow modules defining the desired architecture to reach the interior of the abdomen 4. Other modules can be assembled or disassembled on each rotation module 7 or on each translation module 8, without any class restriction. The forceps module 9 takes up no other modules, and can be mounted on the carrier shaft 5 as first and last module, but also on a rotation module 7 or on a translation module 8.

The architecture of the assembled tool can thus have the required number of degrees of freedom to offer the best dexterity for the doctor in making his surgical gesture. According to a variant, a functional module having several degrees of freedom and also integrating a functional end-piece is feasible. This system of "single module" class 10 will also have a width of less than 12 mm and its architecture will depend of medical needs.

Figure 3:
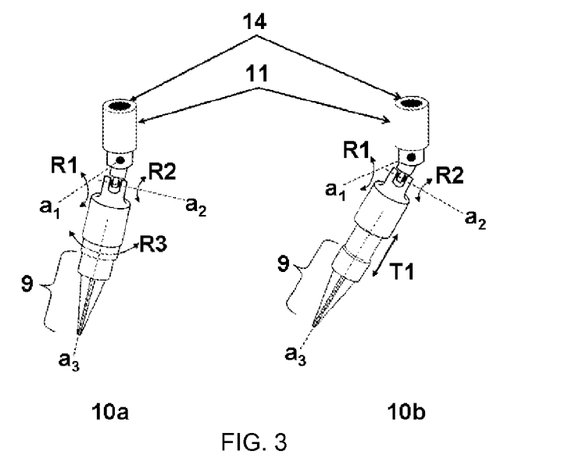
FIG. 3 illustrates two particular functional modules which can be used within the scope of the invention.

FIG. 3 shows the general principle of two modules of the single module class 10; however, the design of this class of modules is not restricted to these two examples of single module. The first module 10a has a configuration of Rotation-Rotation-Rotation-Forceps type where R1, R2 and R3 are rotations which can be made relative to axes a1, a2 and a3, respectively. The second module 10b has a configuration of the type Rotation-Rotation-Translation-Forceps where R1 and R2 are rotations made relative to the axes a1, a2, respectively, and T1 is translation made along the axis a3.

The parts 11 in FIG. 3 are those which will be mounted on the carrier shaft 5 in orifices 14. FIG. 3 shows a forceps module 9 as the final part of each single module 10. As a function of surgical needs and/or of the degree of dexterity required during operation, the system can be updated or reconfigured as required by the surgeon, that is, rotation modules 7 or translation modules 8 can be added or removed.

Figure 4:
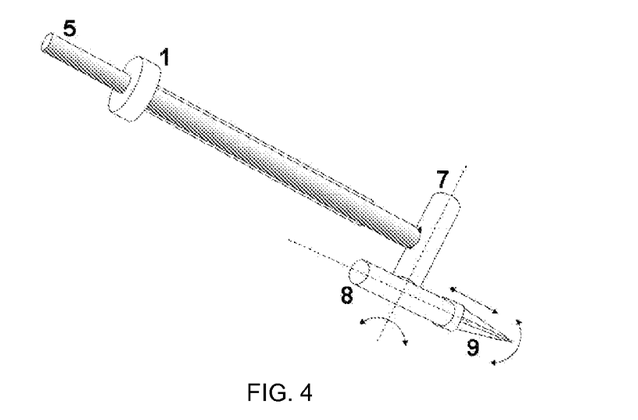
FIG. 4 illustrates an example of an assembled surgical tool.
Figure 5:
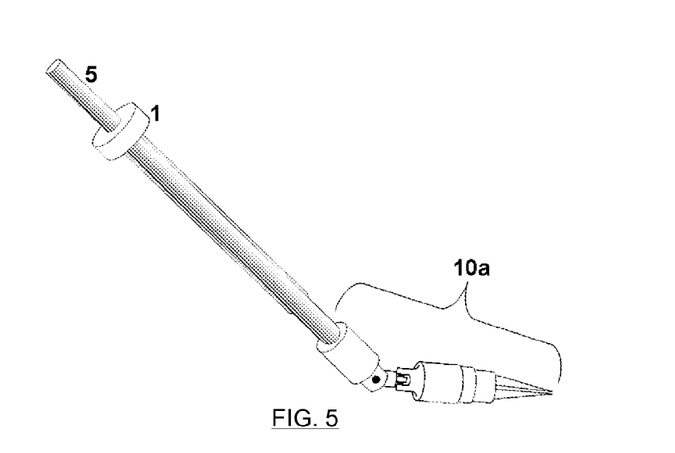
FIG. 5 illustrates another example of an assembled surgical tool.

FIG. 4 illustrates an example of installation at two degrees of freedom, constituted by a rotation module 7, a translation module 8 and a forceps module 9. FIG. 5 illustrates a module 10a of "single module" class mounted on the carrier shaft 5. The recovery of modules of "single module" class 10 will be completed after it has been dismantled from the carrier shaft 5, by one of the means mentioned later in this document.

Figure 6:
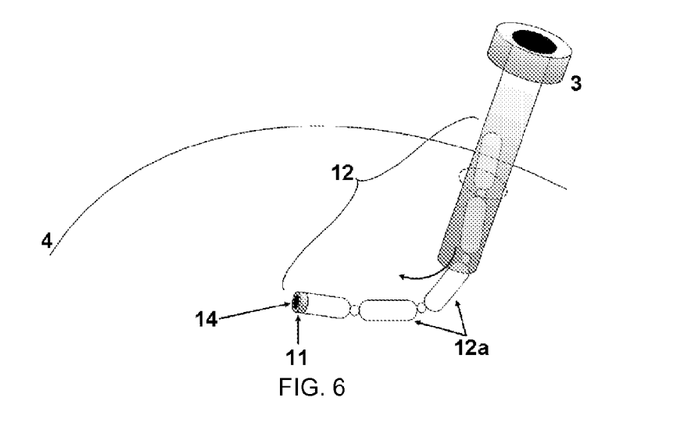
FIG. 6 illustrates another variant of a functional module.

According to another set variant a particular class of single module 12 constituted by a series of independent sub modules 12a as illustrated in FIG. 6 can be provided. This module 12 is also sent to the surgical cavity 4 via the trocar 3. The initial part 11 of this series of sub modules is the part which will be mounted on the carrier shaft (not shown in this figure). Once assembled on the carrier shaft, this module 12 could assume particular configuration of, a priori, any number of possible configurations, as a function of surgical needs.

Figure 7:
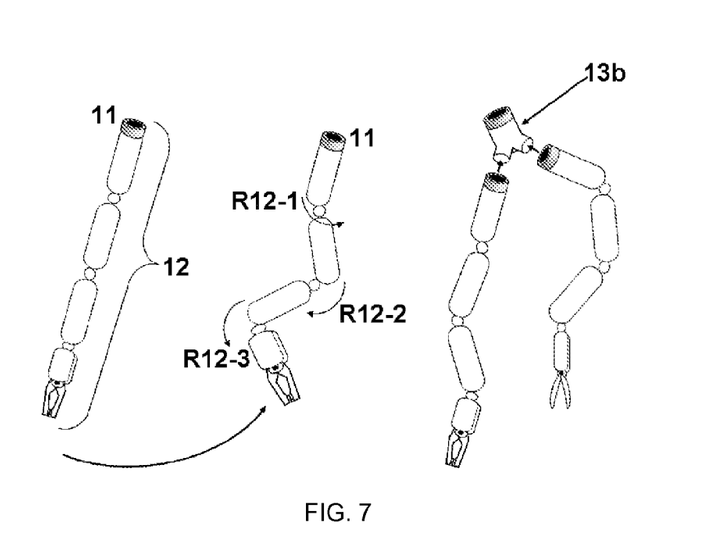
FIG. 7 illustrates several possible configurations of the functional module illustrated in FIG. 6.

So, FIG. 7 illustrates the module 12 in a configuration c1 before and after three rotations R12-1, R12-2 and R12-3 of sub modules. A second configuration c2 of the module 12 is also shown in FIG. 7 where the module 12 has assumed a configuration with two branches, the first bearing forceps at the end of the series of sub modules and the second bearing shears. The surgeon intervenes only in installing the module 12 on the carrier shaft 5. A junction module was designed to increase the number of installations of modules inside the surgical cavity.

Figure 12:
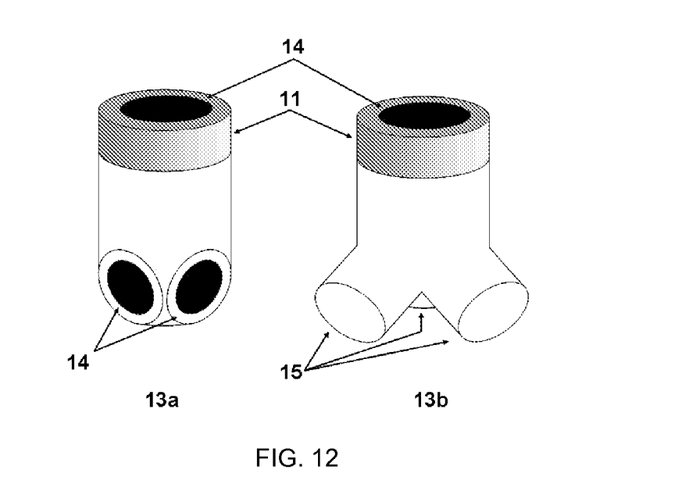
FIG. 12 illustrates two variants of a junction module for increasing the number of degrees of freedom of the surgical tool.

FIG. 12 illustrates two versions of the junction module: a female-female module 13a and a female-male module 13b. The junction module 13a or 13b can take up the various classes of modules 7, 8, 9, 10 or 12. In fact, using the junction module enables multiple installations such as that of two modules 12, illustrated in the right part of FIG. 7 where a junction module 13b (mounted previously in the carrier shaft 5) takes up a first module 12 bearing forceps and a second module 12 bearing shears. Use of the junction module thus increases the number of instruments inside the surgical cavity but without increasing the number of surgical orifices.

The left part of FIG. 7 illustrates the module 12 before and after three rotations R12-1, R12-2 and R12-3 of the sub modules, which defines a change in configuration. These rotations are made inside the surgical cavity after installation of the module 12 in the carrier shaft 5 or in the junction module and are made by way of a command issued outside the surgical cavity. In this case, the surgeon intervenes only in the installation of the module 12 on the carrier shaft 5 or of the junction module on the carrier shaft 5 and the modules 12 on the junction module.

Figure 8:
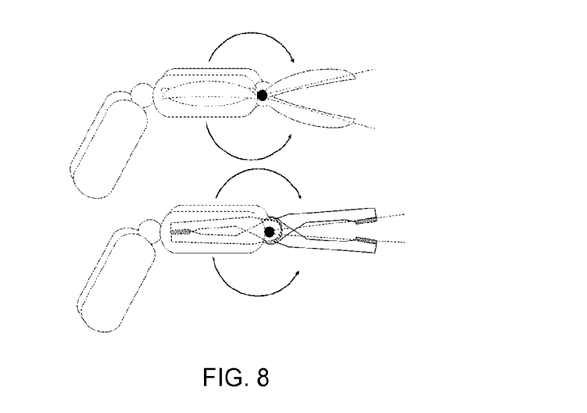
FIG. 8 illustrates two examples of functional end-pieces mounted at the end of the functional module shown in FIGS. 6 and 7.

Relative to the single module 10, the module 12 has a larger number of degrees of freedom due to the number of independent sub modules 12a which constitute it and which can be selected in advance by the doctor; this module 12 is thus redundant. This illustrates an increase in the degree of dexterity of the surgical tool and allows having the preferred mobility according to the operation, without having to change instruments or to add modules. Forceps, shears, etc. of the module 12 are folding tools also forming a sub module, as is illustrated in FIG. 8.

Assembly Process of the Modular Tool

Figure 9:
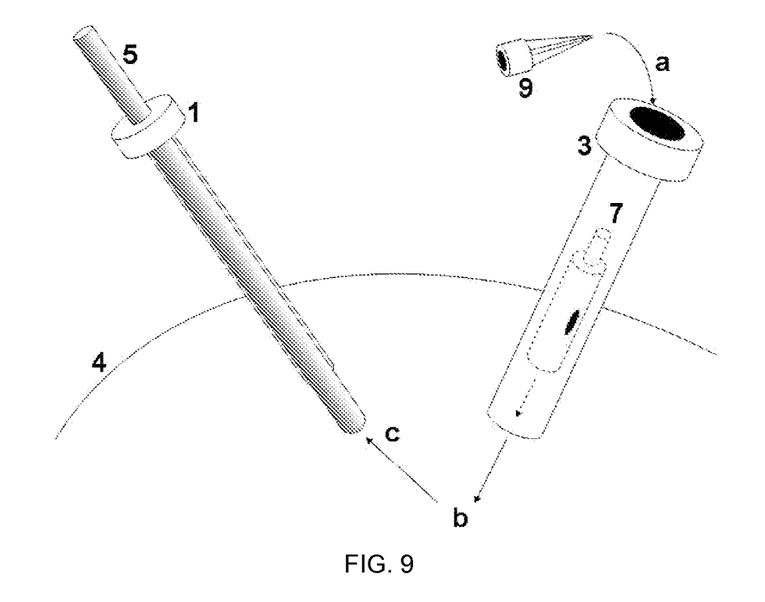
FIG. 9 illustrates the assembly process of the modular surgical tool.

FIG. 9 illustrates the different steps necessary for assembling the tool inside the abdomen. In step (a), the modules are passed through the trocar 3, showing, in dotted lines, a rotation module 7 passing via the trocar 3 and a forceps module 9 about to be inserted into the trocar 3. The modules can be inserted into the interior of the abdomen of the patient for installation of the tool and their recovery after disassembly by using mechanical, magnetic, pneumatic or other means. The modules can be sent to the interior of the abdomen by gravity where they will be recovered for their assembly.

Figure 10:
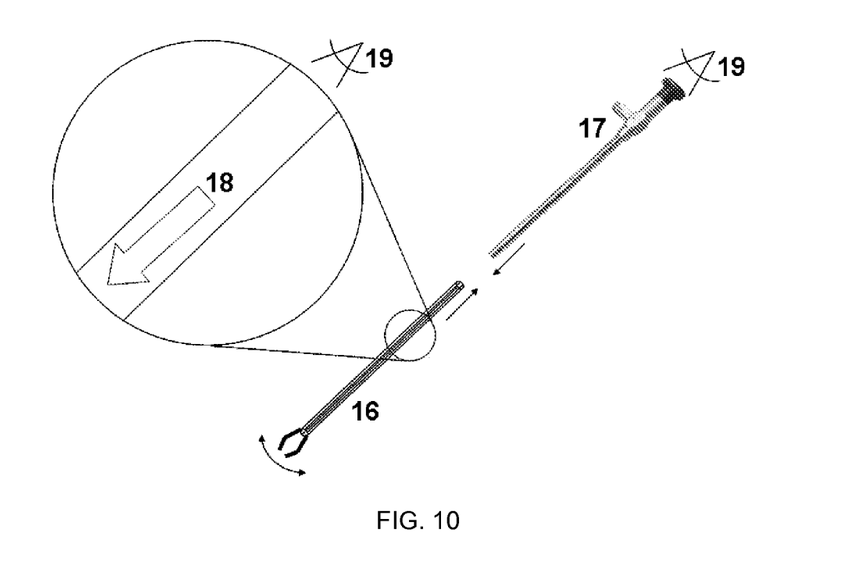
FIG. 10 illustrates an auxiliary device for manipulating functional modules inside the body of the patient.

Step (b) corresponds to recovery of the modules inside the abdomen, for example by using another surgical tool placed in the trocar 2, not shown in this figure. According to another embodiment of the invention, illustrated in FIG. 10, an auxiliary device 16 comprising gripping means for handling the different modules is used. The auxiliary device 16 is for example adapted to the laparoscope 17 without obstructing the visual field 18 of the camera. In fact, this auxiliary device 16 must have well researched architecture to assist locating and handling of modules per region, without interference of the visual field 18. For the assembly phase of the surgical tool, the auxiliary device 16 is mounted on the laparoscope 17 before the first module is sent to the interior of the abdomen and disassembled after completion of assembly of the tool so as not to block the view available for the doctor.

In step (c), the modules are assembled one after the other on the carrier shaft 5, terminating in a forceps module 9. Once assembled, the tool is ready for use in a surgical procedure defined by the surgeon and which does not form the subject matter of the present invention. The number and class of modules to be used as well as the order of installation or configuration of the module depend on the dexterity preferred by the doctor and on the inner space available in the abdomen of the patient.

Any sort of power can be used to actuate the different modules. Selection of the type of power to be used will depend on the medical restrictions for each application and on the technological availability of the moment. The carrier shaft 5 is designed as a function of the nature of the power selected to ensure power supply for all the modules defining the final architecture of the surgical tool. As explained earlier, the means used to provide power and exchange information and control signals between the controller and the functional modules can be conventional means (electric, pneumatic wires, etc.) or else wireless (radio frequency, induction, magnetic, Bluetooth, ultrasound, etc.).

In the case of conventional transmission, the means for connecting each functional module is designed such that they receive and transmit (with the controller and with all modules) information and control signals as well as the required power. Compared to tools of the prior art, the tool according to the invention can accordingly dispense with actuation by cables, which minimises equipment bulk around the surgeon.

Figure 11:
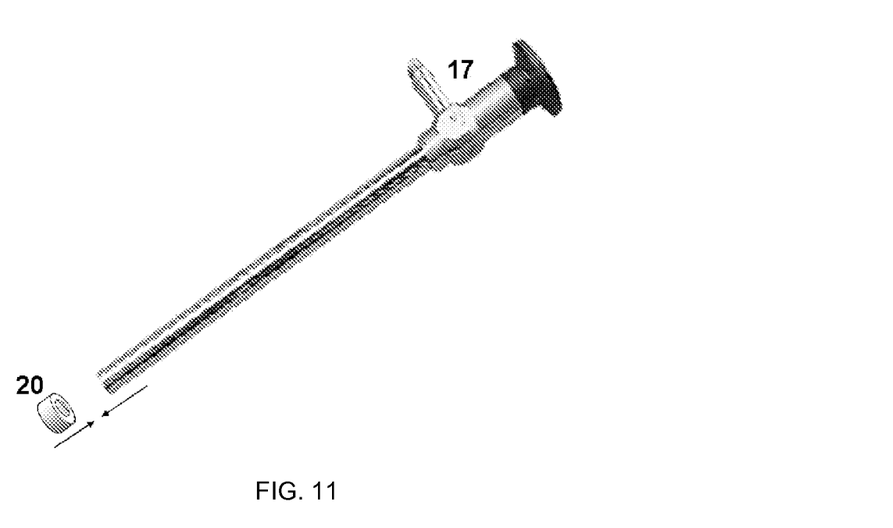
FIG. 11 illustrates another device for manipulation of functional modules.

The tool is disassembled by uninstalling the modules used one by one. The modules are then withdrawn from the interior of the abdomen via the trocar 3. For example, the auxiliary device 16 is mounted on the laparoscope 17 prior to disassembly of the surgical tool and disassembled after all modules have been collected. Other means for recovering the modules from the interior of the abdomen of the patient is a hollow magnet 20 mounted on the laparoscope, as illustrated in FIG. 11.

The orifice of the magnet frees up the visual field of the laparoscope 17. This system recovers the modules one by one by simple contact with the adequate face to guarantee passage through the trocar 3. Other means for depositing and recovering the modules from the interior of the abdomen and for assembling/disassembling them can also be used, such as for example bolt systems, ball-connected systems, clip systems or any other type of connecting system having qualities such as quick installation/disassembly, ease of use and safety. Of these module-recovery means, an endoscopic bag, normally used for extracting part of an organ separated by ablation from the surgical cavity, can also be used.

The materials used for making the different elements such as the carrier shaft 5, the modules 7, 8, 9, 10 12 and 13a or 13b, the auxiliary device 16, the magnet 20 or another connecting device for executing the invention are compatible with sterile and safety conditions required in an operating theatre. The modular tool just described can be used particularly advantageously in relation with the robotic positioning system forming the subject matter of international application WO 03/094 579. The proximal end of the carrier shaft 5 is attached to appropriate support means. In this way, the surgeon can benefit from the functionalities and minimal bulk of such a robotic system, while benefiting from all degrees of freedom allowed by the modular tool.

Of course, the dimensions of the trocars have been given by way of example, given that trocars of larger diameter can be used to allow passage of larger modules. Finally, the invention has been described within the scope of laparoscopy, where the surgical cavity is the abdomen, but it is understood that it applies to all interventions feasible in minimally invasive surgery.

The invention claimed is:

1. A minimally invasive surgical intervention device, comprising a set defining a modular surgical tool, the set comprising a carrier shaft and a plurality of functional modules, in which each of the functional modules has a connecting end fitted to the carrier shaft and to another functional module, and has appropriate dimensions for insertion into a body of a patient via a trocar, wherein:

each functional module has at least one of (i) a degree of freedom in rotation, (ii) a degree of freedom in translation, and (iii) a functional end-piece including one of: forceps, a hook, and a scalpel;

at least one of: the carrier shaft and the functional modules are designed so as to actuate the functional modules according to at least one of: their degree of freedom and their respective function;

the set further comprises a junction module configured to couple the carrier shaft to at least two of the functional modules in a branching manner, wherein the junction module has at least three connecting ends that are each fitted to at least one of the carrier shaft and the at least two functional modules;

the set further comprises an electromechanical interface controlling the actuation of the installed functional modules which define the tool; and the connecting end of each of the functional modules is reversibly fitted to the carrier shaft.

2. The device as claimed in claim 1, wherein:

the functional modules provide a degree of freedom in rotation, and a degree of freedom in translation.

3. The device as claimed in claim 1 wherein the connecting end of each of the functional modules includes either a male or female connecting form.

4. The device as claimed in claim 1, wherein at least one of the functional modules comprises the functional end-piece, and the functional end-piece includes forceps.

5. The device as claimed in claim 1, wherein each of the functional modules is reversibly attached to another of the functional modules independent of the carrier shaft.

6. The device as claimed in claim 1, wherein at least one of the functional modules comprises the functional end-piece.

7. The device as claimed in claim 1, wherein the connecting end of each functional module is reversibly attachable to another functional module which includes a battery powered actuator.

8. The device as claimed in claim 1, wherein the connecting end of each functional module is reversibly attachable to another functional module independent of the carrier shaft.

9. The device as claimed in claim 1, wherein at least one of the functional modules comprises an actuator member configured to actuate the at least one functional module according to at least one of: its degree of freedom and its function.

10. The device as claimed in claim 1, wherein at least one of the functional modules has a degree of freedom in at least one of rotation and translation, and the device further comprises an actuator member configured to actuate the at least one functional module according to its degree of freedom using at least one of electrical power, hydraulic power, and pneumatic power.

11. The device as claimed in claim 1, further comprising an actuator member configured to actuate the functional modules relative to one another without using a cable.

12. The device as claimed in claim 1, further comprising magnetism connects together the functional modules.

13. The device as claimed in claim 1, wherein the functional modules are adapted for assembly and disassembly within a patient's surgical cavity.

14. The device as claimed in claim 1, wherein the carrier shaft has a diameter less than or equal to 8 mm, and each of the functional modules has at least one dimension less than or equal to 12 mm.

15. The device as claimed in claim 1, further comprising a handling member operable to handle each of the functional modules in the body of the patient, wherein the handling member comprises forceps connected to an imaging device.

16. The device as claimed in claim 15, wherein the handling member comprises a magnet having a hollow cylindrical shape and capable of being mounted on the imaging device without blocking a visual field of the imaging device.

17. The device as claimed in claim 1, comprising the trocar having an inner diameter less than or equal to 8 mm for the insertion of the shaft and a second trocar having an inner diameter less than or equal to 12 mm for inserting the functional modules.

18. The device as claimed in claim 1, wherein at least one of the functional modules comprises the functional end-piece, and the functional end-piece includes a scalpel.

19. The device as claimed in claim 1, wherein the functional modules are cylindrically shaped.

20. The device as claimed in claim 1, wherein the functional modules are cube shaped.

21. The device as claimed in claim 1, wherein each of the functional modules includes an orifice at the connecting end.

* * * * *